United States Patent
Gehling et al.

(10) Patent No.: US 7,341,737 B2
(45) Date of Patent: Mar. 11, 2008

(54) MEDICATED TAMPON

(75) Inventors: Steven Craig Gehling, Oshkosh, WI (US); Donald C. Harrison, Indian Hill, OH (US); James H. Liu, Bratenahl, OH (US); Wolfgang A. Ritschel, Cincinnati, OH (US); Chris Clendening, Cleves, OH (US); Giovanni M. Pauletti, Loveland, OH (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/335,759

(22) Filed: Dec. 31, 2002

(65) Prior Publication Data

US 2003/0144639 A1    Jul. 31, 2003

Related U.S. Application Data

(63) Continuation-in-part of application No. 09/626,025, filed on Jul. 27, 2000, now Pat. No. 6,572,874, which is a continuation-in-part of application No. 09/079,897, filed on May 15, 1998, now Pat. No. 6,197,327.

(60) Provisional application No. 60/347,719, filed on Jan. 10, 2002, provisional application No. 60/049,325, filed on Jun. 11, 1997.

(51) Int. Cl.
*A61F 13/02* (2006.01)
*A61F 9/02* (2006.01)
*A61F 13/20* (2006.01)

(52) U.S. Cl. ............ 424/431; 424/430; 424/433; 424/436; 424/729; 424/732; 424/744; 424/754; 424/757; 424/767; 514/966; 514/967; 604/358; 604/604

(58) Field of Classification Search .............. 424/422, 424/430, 431, 436, 729, 732, 744, 754, 757, 424/767; 604/358, 904; 514/966, 967
See application file for complete search history.

(56) References Cited

U.S. PATENT DOCUMENTS

| 1,395,295 A | * | 11/1921 | Pond | .................. 604/287 |
| 3,338,992 A | | 8/1967 | Kinney | |
| 3,341,394 A | | 9/1967 | Kinney | |
| 3,502,538 A | | 3/1970 | Petersen | |

(Continued)

FOREIGN PATENT DOCUMENTS

EP    0 110 793 A2    6/1984

*Primary Examiner*—Sreeni Padmanabhan
*Assistant Examiner*—Konata M. George
(74) *Attorney, Agent, or Firm*—Denise I Stoker; Sebastian C. Pugliese; Randall W. Fieldhack

(57) ABSTRACT

A tampon adapted to deliver a therapeutic agent, the tampon including a tampon body having a distal end; and a dosage form affixed to the distal end of the tampon body, wherein the dosage form includes a formulation including a therapeutic agent, and wherein the dosage form comprises a plurality of layers. Also, a method for manufacturing a medicated tampon adapted to deliver a therapeutic agent, the method including manufacturing a tampon body having a distal end; producing a dosage form having a plurality of layers, wherein the dosage form includes a formulation including a therapeutic agent; and affixing the dosage form to the distal end of the tampon body.

30 Claims, 1 Drawing Sheet

U.S. PATENT DOCUMENTS

| | | |
|---|---|---|
| 3,502,763 A | 3/1970 | Hartmann |
| 3,542,615 A | 11/1970 | Dobo et al. |
| 3,595,236 A | 7/1971 | Corrigan et al. |
| 3,692,618 A | 9/1972 | Dorschner et al. |
| 3,796,219 A * | 3/1974 | Hanke .................. 604/48 |
| 3,802,817 A | 4/1974 | Matsuki et al. |
| 3,849,241 A | 11/1974 | Butin et al. |
| 4,317,447 A | 3/1982 | Williams ................ 128/260 |
| 4,318,405 A | 3/1982 | Sneider ................ 128/263 |
| 4,340,563 A | 7/1982 | Appel et al. |
| 4,488,928 A | 12/1984 | Ali Khan et al. |
| 4,582,717 A | 4/1986 | Von Bittera et al. ............ 427/2 |
| 5,641,503 A | 6/1997 | Brown-Skrobot |
| 6,126,959 A * | 10/2000 | Levine et al. .............. 424/434 |
| 6,758,840 B2 | 7/2004 | Knox |
| 2003/0114394 A1* | 6/2003 | Levine et al. .............. 514/26 |
| 2003/0139709 A1 | 7/2003 | Gehling |
| 2003/0143278 A1* | 7/2003 | DiPiano et al. ............ 424/489 |
| 2004/0044080 A1* | 3/2004 | Place et al. ................ 514/573 |

\* cited by examiner

MEDICATED TAMPON

CROSS-REFERENCE TO RELATED APPLICATION

This application is a continuation-in-part of application Ser. No. 09/626,025, filed Jul. 27, 2000, issued as U.S. Pat. No. 6,572,874, which is a continuation-in-part of the U.S. patent application Ser. No. 09/079,897, filed on May 15, 1998, issued as U.S. Pat. No. 6,197,327, which claims priority of the Provisional Application Ser. No. 60/049,325, filed Jun. 11, 1997, under 35 U.S.C. §111(b). This application also claims the benefit of U.S. Provisional Application No. 60/347,719, filed Jan. 10, 2002, herein incorporated by reference.

BACKGROUND

This invention pertains to a method of manufacturing delivery devices used for the application of various vaginal therapeutic treatments or other non-medicinal vaginal preparations into the vaginal cavity.

Many disease states and physiological conditions can occur in a woman, including symptoms associated with premenstrual syndrome, menstruation, and menopause. These symptoms may include dysmenorrhea (menstrual cramping), irritability, water retention, moodiness, depression, anxiety, skin changes, headaches, breast tenderness, tension, weight gain, cravings, fatigue, and hot flashes. Symptoms of conditions can include itching and other associated sensory maladies.

Many of these symptoms are due to changes in hormonal levels throughout the menstrual cycle. Menstrual cramping is associated with increased levels of prostaglandin F2$\alpha$, prostaglandin E2, and in some cases leukotrienes in the endometrium and menstrual fluid. These eicosinoids lead to restricted blood flow to the uterus and increased uterine contractions, causing pain.

One example is dysmenorrhea, which is the occurrence of painful uterine cramps during menstruation that affects a large number of post-pubescent women. The pain of dysmenorrhea originates in the uterus. Various analgesics can be effective in limiting the pain from dysmenorrhea; some have used orally-delivered analgesics, while others have searched for alternative analgesic delivery methods.

Attempts have been made to deliver analgesics in the vicinity of the cervix and the vaginal mucosa using various vaginally-inserted devices and methods. Because many of these symptoms typically occur in conjunction with menstruation, some have tried to combine an analgesic with a tampon.

Constant mixing of the heated combination is required to produce a homogeneous compound. As the combination cools, the ingredients solidify into a solid waxy substance that is securely fastened to the tip of the tampon.

SUMMARY OF THE INVENTION

Several problems are inherent in a process that attempts to introduce a therapeutic agent into or onto a tampon by coating, dipping, solidifying, or the like. Procedures such as these that may work in a laboratory setting may be precluded from application to an automated tampon manufacturing process. Because of stringent dosing requirements, the therapeutic agent and its carrier must be maintained in a solution that is both homogeneous and at a proper concentration and purity. These requirements are difficult to accomplish during normal operation, and are significantly more difficult to maintain when the tampon machine stops. In addition, tampons of different densities will absorb an applied liquid therapeutic agent differently, resulting in variability in agent absorption into the tampons across different tampons.

Specifically, the requirement to provide constant agitation or mixing of the ingredients to the excipient and active compounds raises concerns as to how to keep the solid active ingredient homogeneously suspended in a solution when the tampon machine stops during normal operation cycling. The use of inline mixers and recirculation of the heated therapeutic and excipient contained liquid compounds during machine stops may provide a method to keep the solution moving and mixed. However, because a machine could be stopped for several hours, the stability of some compound mixtures may be compromised by long durations at elevated temperatures, or by mechanical shear forces due to the continuous pumping of the recirculating solution.

The invention described herein provides a tampon adapted to deliver a therapeutic agent, the tampon including a tampon body having a distal end; and a dosage form affixed to the distal end of the tampon body, wherein the dosage form includes a formulation including a therapeutic agent, and wherein the dosage form comprises a plurality of layers.

The invention described herein also provides a method for manufacturing a medicated tampon adapted to deliver a therapeutic agent, the method including manufacturing a tampon body having a distal end; producing a dosage form having a plurality of layers, wherein the dosage form includes a formulation including a therapeutic agent; and affixing the dosage form to the distal end of the tampon body.

The invention described herein resolves these problems by incorporating a dosage form onto a tampon to form a medicated tampon. In one embodiment, all or a portion the dosage form is slightly activated by an energy source, so that the carrier component will be allowed to interact with, and bond securely to, the tampon. The dosage form is sufficiently stable and may be manufactured separately in a controlled facility, whereby dose is easily controlled through controls on homogeneity, concentration, and purity.

The advantages of an assembly type process using a pre-manufactured dosage form over a continuous in-line process where the medicated ingredients are applied to the tampon coincident with the tampon manufacturing process are numerous. The dosage form would be desirably produced at a qualified pharmaceutical manufacturer, which could ensure that the correct dose and purity of the active ingredient is homogeneously dispersed within the dosage form, or homogeneously dispersed within each layer of the dosage form. The use of dosage forms would simplify the modifications to an existing tampon manufacturing process. The use of dosage forms would allow multiple types of therapeutic agents to be applied to the tampon. The chemical and physical stabilities of the dosage form are not compromised by the assembly process onto the tampon. The process is less dependent on the physical characteristics of the absorbent structure of the tampon, because only a partial phase change of the excipient ingredient(s) is required to bond with the tampon. Finally, product costs of this disclosed invention would also be advantageous because the medicated tampon is compatible with existing manufacturing processes.

This invention describes a therapeutic agent delivery system in cooperation with a feminine care product by providing a therapeutic agent delivery system that is integral with or associated with the feminine care product. The therapeutic agent delivery system including the therapeutic agent and carrier components can be any therapeutic agent that will be absorbed into the body through the vaginal epithelium, or deposited topically on the vaginal epithelium, for the purposes of treating a physiological disease, state, or condition.

Other objects and advantages of the present invention will become more apparent to those skilled in the art in view of the following description and the accompanying drawings.

DETAILED DESCRIPTION OF THE PREFERRED EMBODIMENTS

Figure 1:
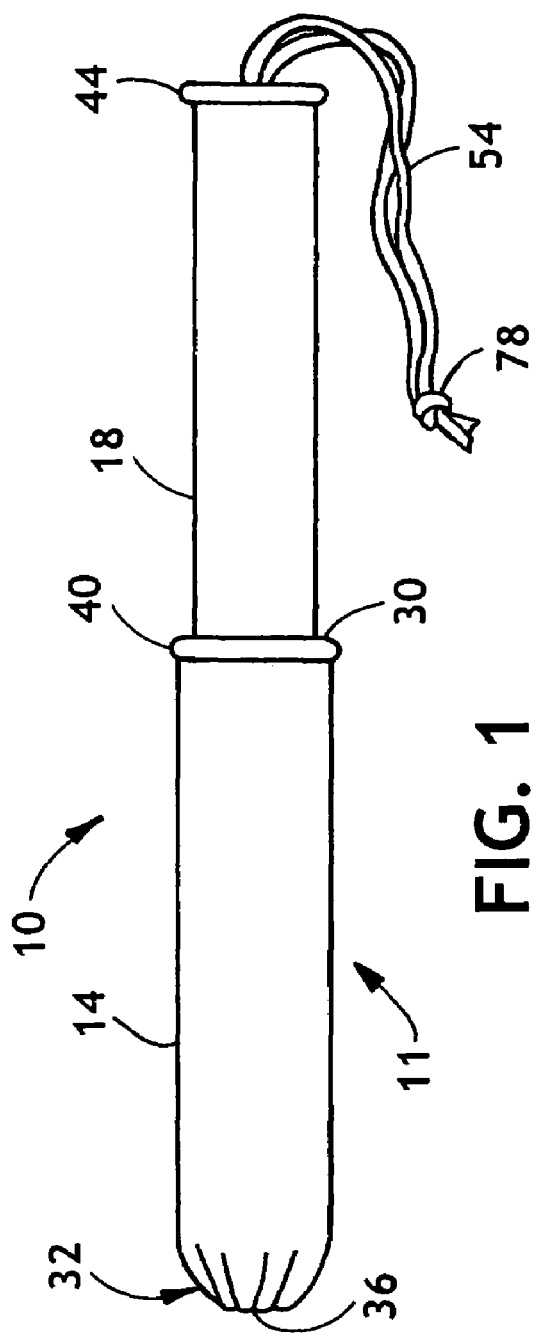
FIG. 1 is a perspective view of a two-piece tampon applicator.

The invention as described herein will be described for exemplary purposes using a tampon as an example of a feminine care product. The invention, however, applies equally to other forms of products, including tampon-like devices and vaginally-inserted devices, and should not be limited to the example described herein. Also contemplated is the use of the invention described herein in conjunction with non-catamenial feminine products such as incontinence products, including female incontinence inserts.

As used herein the term "nonwoven fabric or web" means a web having a structure of individual fibers or threads that are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, and bonded carded web processes. The basis weight of nonwoven fabrics is usually expressed in ounces of material per square yard ("osy") or grams per square meter ("gsm") and the fiber diameters useful are usually expressed in microns. Basis weights can be converted from osy to gsm simply by multiplying the value in osy by 33.91.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. Nos. 4,340,563; 3,692,618; 3,802,817; 3,338,992; 3,341,394; 3,502,763; 3,502,538; and 3,542,615. Spunbond fibers are quenched and generally not tacky when deposited onto a collecting surface. Spunbond fibers are generally continuous and have average diameters frequently larger than 7 microns, typically between about 10 and 20 microns.

As used herein the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly disbursed meltblown fibers. Such a process is disclosed, for example, in U.S. Pat. No. 3,849,241. Meltblown fibers are microfibers that may be continuous or discontinuous and are generally smaller than 10 microns in average diameter.

As used herein "bonded carded webs" or "BCW" refers to nonwoven webs formed by carding processes as are known to those skilled in the art and further described, for example, in U.S. Pat. No. 4,488,928 which is incorporated herein by reference. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer shall include all possible geometrical configurations of the material. These configurations include, but are not limited to isotactic, syndiotactic, and random symmetries.

As used herein, the term "hydrophilic" means that the polymeric material has a surface free energy such that the polymeric material is wettable by an aqueous medium, i.e. a liquid medium of which water is a major component. The term "hydrophobic" includes those materials that are not hydrophilic as defined. The phrase "naturally hydrophobic" refers to those materials that are hydrophobic in their chemical composition state without additives or treatments affecting the hydrophobicity. It will be recognized that hydrophobic materials may be treated internally or externally with treatments such as surfactants and the like to render them hydrophilic.

As used herein, the term "surface" and its plural generally refer herein to the outer or the topmost boundary of an object.

As used herein, the phrase "absorbent article" refers to devices which absorb and contain body fluids, and more specifically, refers to devices which are placed against or near the skin, or against or near the vaginal vault epithelium, to absorb and contain the various fluids discharged from the body.

As used herein, the term "disposable" is used herein to describe absorbent articles that are consumable and not intended to be laundered or otherwise restored or reused as an absorbent article after a single use.

As used herein, the term "dosage form" is used herein as a generic term for a drug form including a formulation including a therapeutic agent. The drug form may be a dosage in the form of a suppository, a capsule or any other suitable form. The drug form may also be spherical, ovoid, domal, frustoconical, generally flat, or any other suitable shape dictated by the needs of the application of the drug form. The drug form may have convex, concave, planar, arcuate, or any other suitable surfaces as dictated by the needs of the application of the drug form.

Figure 2:
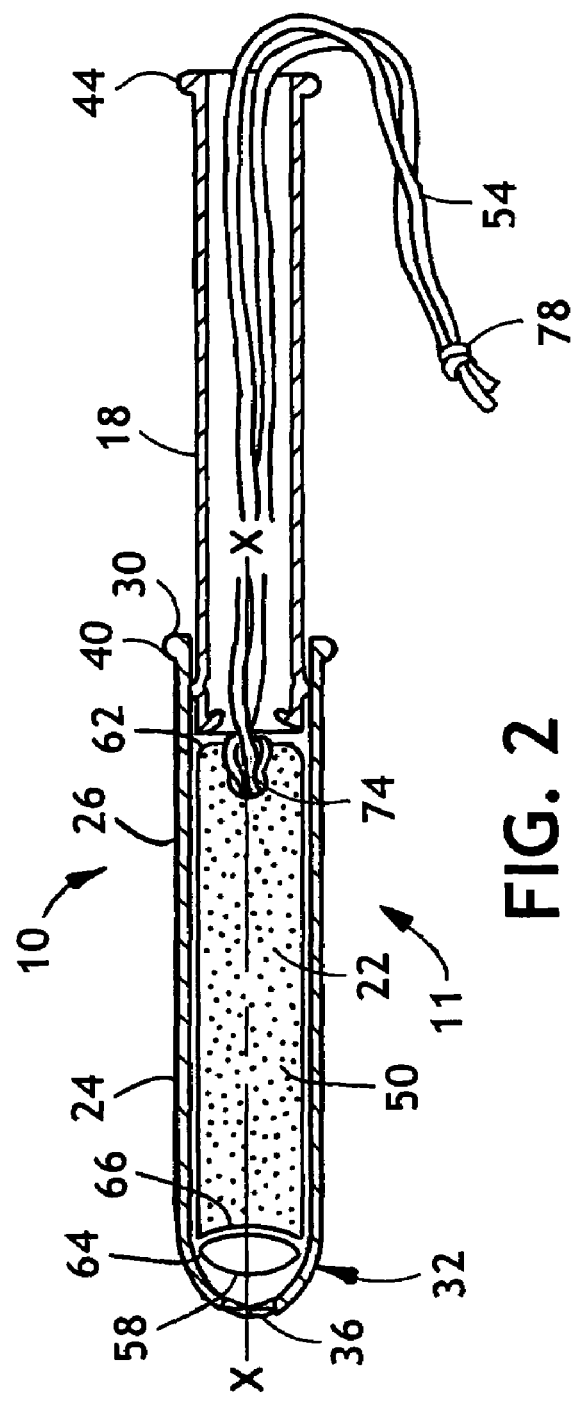
FIG. 2 is a cross-sectional view of the tampon applicator shown in FIG. 1.

FIGS. 1-2 illustrate a tampon applicator 11, including a first member 14 and a second member 18, which is designed to house a catamenial tampon 22 and provide a comfortable means of inserting the tampon 22 into a woman's vagina.

The tampon applicator 11 includes a first member 14 and a second member 18. The first member 14 can be in the form of a spirally wound, convolutely wound or longitudinally seamed hollow tube which is formed from paper, paperboard, cardboard or other suitable material, or a combination thereof. The first member 14 can also be in the form of a seamless plastic tube. Any plastic in the first member 14 is preferably polyethylene, but may be polypropylene or other suitable plastic. The first member 14, also commonly referred to as an outer tube, can be of any suitable dimensional arrangement. For example, the first member 14 may be fairly rigid and have a relatively small diameter of about 10 mm to about 20 mm.

The first member 14 has a wall 24 that may have a predetermined thickness of about 0.2 mm to about 0.6 mm. When the first member 14 is spirally wound, convolutedly wound, or longitudinally wound, the wall 24 can be constructed from a single ply of material or be formed from two or more plies which are bonded together to form a laminate. The use of two or more plies or layers enables the manufacture to use certain material in the various layers that can enhance the performance of the tampon applicator 11. When two or more plies are utilized, all the plies can be spirally wound, convolutely wound or longitudinally seamed to form an elongated cylinder. The wall 24 can be constructed using a smooth thin ply of material on the outside or exterior surface 26 which surrounds a coarser and possibly thicker ply. When the wall 24 contains at least three plies, the middle ply can be the thicker ply and the interior and exterior plies can be smooth and/or slippery to facilitate expulsion of the tampon 22 and to facilitate insertion of the first member 14 into a woman's vagina, respectively. By sandwiching a thick, coarser ply of material between two thin, smooth plies, an inexpensive first member 14 can be provided that is very functional. The wall 24 should contain one to four plies, although more plies can be utilized if desired.

The plies forming the wall 24 can be held together by an adhesive, such as glue, or by heat, pressure, ultrasonics, etc. The adhesive can be either water-soluble or water-insoluble. A water-soluble adhesive is preferred for environmental reasons in that the wall 24 will quickly break apart when it is immersed in water. Such immersion will occur should the first member 14 be disposed of by flushing it down a toilet. Exposure of the first member 14 to a municipal's waste treatment plant wherein soaking in water, interaction with chemicals, and agitation all occur will cause the wall 24 to break apart and even dissolve in a relatively short period of time.

The inside diameter of the first member 14 is usually less than about 0.75 inches (about 19 mm) and preferably less than about 0.625 inches (about 16 mm). Although the exterior diameters of tampons vary, most tampons utilized by women have an external diameter of less than about 0.75 inches (about 19 mm).

The first member 14 is sized and configured to house the absorbent tampon 22. As stated above, the first member 14 should have a substantially smooth exterior surface 26 which will facilitate insertion of the first member 14 into a woman's vagina. When the exterior surface 26 is smooth and/or slippery, the first member 14 will easily slide into a woman's vagina without subjecting the internal tissues of the vagina to abrasion. The first member 14 can be coated to give it a high slip characteristic. Wax, polyethylene, a combination of wax and polyethylene, cellophane and clay are representative coatings that can be applied to the first member 14 to facilitate comfortable insertion.

The first member 14 can be a straight, elongated cylindrical tube formed on a central longitudinal axis X-X (see FIG. 2). It is also possible to form the first member 14 into an arcuate shape. The arcuate or curved shape can assist in providing comfort when inserting the first member 14 into a woman's vagina. With a curved tampon applicator, it is possible to employ a curved tampon which again may be more comfortable for some women to use since the shape of the tampon may better fit the curvature of a woman's vagina.

Referring to FIG. 1, an insertion tip 32 is shown having a plurality of pleats or petals 36 that can radially open such that the insertion tip 32 has a diameter approximately equal to or greater than the diameter of the first member 14. The pleats 36 can be either even or odd in number and can be equally spaced apart or non-uniformly arranged.

Referring again to FIGS. 1 and 2, the first member 14 can have a fingergrip ring 40 located approximate the second end 30. The fingergrip ring 40 can be integrally formed from the material from which the first member 14 is constructed or it can be a separate member that is secured in place by an adhesive or some other type of attachment mechanism. The fingergrip ring 40 functions to provide a means for the user to grip the first member 14 and hold it between her thumb and middle finger. The user can then position her forefinger on the free end of the second member 18 and orient the first member 14 relative to her vagina while she pushes the second member 18 into the first member 14.

As stated above, the tampon applicator 11 includes a second member 18, also commonly referred to as an inner tube. The second member 18, like the first member 14, can be a spirally wound, a convolutely wound or a longitudinally seamed hollow tube constructed from paper, paperboard, cardboard, or other suitable material, or a combination thereof. The second member 18 can also be in the form of a seamless plastic tube. Any plastic in the second member 18 is preferably polyethylene, but may be polypropylene or other suitable plastic. The second member 18 can be constructed of the same material as the first member 14 or it can be made out of a different material. The second member 18 may also be a solid stick or use some other unique shape. It is also possible to form a fingergrip ring or flange 44 on the outer end of the second member 18 to provide an enlarged surface onto which the user's forefinger can rest. The fingergrip ring 44 thereby functions as a seat for the forefinger and facilitates movement of the second member 18 into the first member 14.

In an alternate embodiment (not shown), the first member 14 and second member 18 of the tampon applicator 11 may be replaced by a stick applicator. The stick applicator is used to insert the tampon 22, after which the stick applicator is withdrawn.

A tampon 22 is an absorbent member primarily designed to be worn by a woman during her menstrual period to absorb menses, blood and other body fluid. The tampon 22 includes a tampon body 50 and a withdrawal string 54. The tampon body 50 is normally compressed into the form of a cylinder and can have a blunt, rounded or shaped distal or tip end 58. The tampon body 50 has a distal end 58 that is closer to the cervix when the tampon 22 is in use. The tampon body 50 also has a proximal or string end 62 that is closer to the vaginal opening when the tampon 22 is in use.

The tampon 22 commonly has a withdrawal string 54 fastened to the proximal end 62 that serves as a means for withdrawing the tampon from the woman's vagina. The withdrawal string 54 can be looped through an aperture 74 formed transversely through the tampon body 50. In addition, the withdrawal string 54 can have a knot 78 formed at the free end of the string to assure that the string 54 will not separate from the tampon body 50.

Catamenial tampons suitable for use in the present invention include an absorbent material. The absorbent material can be formed from fibers that are assembled into an absorbent sheet or ribbon. Alternatively, the absorbent material can be formed from absorbent fibers that are assembled and compressed into a generally elongated and/or cylindrical configuration. The absorbent material is desirably formed from natural cellulosic fiber, such as cotton and rayon. For example, the absorbent material can be 100% cotton, 100% rayon, a blend of cotton and rayon fibers, or other materials known to be suitable for tampons, including artificial fibers such as polyester, polypropylene, nylon or blends thereof. The absorbent material may also include degradable fibers. Other types of materials or structures may also be used, such as cellulose sponge or a sponge formed from elastomeric materials. When formed, the absorbent material typically includes interstitial space or voids between the fibers or other materials.

Tampons suitable for use in this invention are usually made of absorbent fibers, including one or both of natural and synthetic fibers, compressed into a unitary body of a size that may easily be inserted into the vaginal cavity. Fiber orientation is typically in a linearly- or radially-wound structure. Tampons are normally made in an elongated cylindrical form in order that they may have a sufficiently large body of material to provide the required absorbing capacity, but may be made in a variety of shapes. The tampon 22 is typically compressed. Compression may be achieved by predominantly longitudinally-, axially-, or radially-applied pressure, or a combination thereof. The tampon 22 may be made of various fiber blends including both absorbent and nonabsorbent fibers, which may or may not have a suitable cover or wrapper. The cover or wrapper for absorbent products, such as tampons and sanitary napkins, is often made from a sheet of nonwoven fibers, e.g., a spunbond polypropylene sheet. The tampon may also include one or more of various treatments to improve the performance of the tampon, including reduced friction and increased absorption, delivery of the therapeutic agent, or a combination of treatments.

The fibers from which the present absorbent products are made may be produced, for example, by the meltblowing or spunbonding processes, including those producing bicomponent, biconstituent, or polymer blend fibers that are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are microfibers as defined above. The manufacture of spunbond and meltblown webs is discussed generally above.

As mentioned, the nonwoven also may be a bonded carded web. Bonded carded webs are made from staple fibers, which are usually purchased in bales. The bales are placed in a picker, which separates the fibers. The fibers are sent through a combing or carding unit, which further breaks apart and aligns the staple fibers in the machine direction to form a generally machine direction-oriented fibrous nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable bonding method, particularly when using bicomponent staple fibers, is through-air bonding.

An exemplary absorbent material is a nonwoven web composed of 3.0 denier polyethylene sheath/polypropylene core bicomponent staple fibers having a length of 38 millimeters. Such bicomponent fibers can be obtained from Chisso Corporation and are typically supplied with a vendor fiber finish or other treatments. The staple fibers can be sent through an opener and uniformly mixed together before being carded into a web at a line speed of 15.24 meters per minute (50 feet per minute). Once the web is formed, it can be sent through a through-air bonder (drum type) with an air temperature of 131° C. Typical dwell times within the bonder are between 3 and 4.5 seconds. The resultant web, which has a basis weight of 100 gsm and a density of 0.06 gm/cm$^3$, can then be wound up on a roll.

A therapeutic agent delivery system 10 including a therapeutic agent can be produced including the tampon 22. For the purposes of this invention, any therapeutic agent that will be absorbed into a user's body through the vaginal epithelium for the purposes of treating diseases or conditions such as, for example, dysmenorrhea, can be used. Alternatively, or in addition, therapeutic and other beneficial agents such as vitamins, hormones, moisturizers, antifungal agents, antibacterial agents, pro-biotic agents that promote the growth of normal vaginal bacterial flora, and the like may be similarly delivered.

Therapeutic agents for use in the invention are absorbable through the vaginal epithelium and travel to the uterus by a unique portal of veins and arteries which are known to exist between the vagina, the cervix and the uterus. This anastomosis eliminates so called first pass metabolism by the liver, effectively delivering higher concentrations of therapeutic agent to the uterus than would otherwise be available via oral dosing. One skilled in the art knows the efficacy of therapeutic agents in such an application when introduced at a particular anatomical location. For example, when the therapeutic agent is selected to treat dysmenorrhea, it preferably is selected from nonsteroidal anti-inflammatory drugs (NSAIDs), prostaglandin inhibitors, COX-2 inhibitors, local anesthetics, calcium channel blockers, potassium channel blockers, β-adrenergic agonists, leukotriene blocking agents, smooth muscle inhibitors, and drugs capable of inhibiting dyskinetic muscle contraction.

COX-2 inhibitors, such as Celecoxib, Meloxicam, Rofecoxib, and Flosulide are novel anti-inflammatory and analgesic compounds. These compounds effectively inhibit production of COX-2 (cyclooxygenase-2) enzyme that is induced by pro-inflammatory stimuli in migratory cells and inflamed tissue. Because COX-2 is also involved in reproductive processes, selective COX-2 inhibitors will reduce uterine contractions in pre-term labor and relieve painful uterine contractions associated with dysmenorrhea by blocking prostaglandin receptors in the uterus. Additionally, they may reduce endometrial bleeding.

Preferred NSAIDs include aspirin, ibuprofen, indomethacin, phenylbutazone, bromfenac, sulindac, nabumetone, ketorolac, mefenamic acid, and naproxen. Preferred local anesthetics include lidocaine, mepivacaine, etidocaine, bupivacaine, 2-chloroprocaine hydrochloride, procaine, and tetracaine hydrochloride. Preferred calcium channel antagonists include diltaizem, israpidine, nimodipine, felodipine, verapamil, nifedipine, nicardipine, and bepridil. Preferred potassium channel blockers include dofetilide, e-4031, imokalant, sematilide, ambasilide, azimilide, tedisamil, rp58866, sotalol, piroxicam, and ibutilide. Preferred β-adrenergic agonists include terbutaline, salbutamol, metaproterenol, and ritodrine. Vasodilators, which are believed to relieve muscle spasm in the uterine muscle, include nitroglycerin, isosorbide dinitrate, and isosorbide mononitrate.

Examples of beneficial botanicals may include, but are not limited to, *Agnus castus*, aloe vera, comfrey, calendula, dong quai, black cohosh, chamomile, evening primrose, *Hypericum perforatum*, licorice root, black currant seed oil, St. John's wort, tea extracts, lemon balm, capsicum, rosemary, *Areca catechu*, mung bean, borage seed oil, witch hazel, fenugreek, lavender, and soy. *Vaccinium* extracts commonly derived from many members of the heath family, cranberries such as blueberries, and azaleas (*Rhododendron* spp.) as well as from red onion skin and short and long red bell peppers, *Beta vulgaris* (beet) root extract, and capsanthin may also be used. Other berries that have applicability are whortleberry, lingenberry, chokeberry, sweet rowan, rowanberry, seabuckhrouberry, crowberry, strawberries, and gooseberries.

Other beneficial agents that may be used include, but are not limited to, vitamins, calcium, magnesium, hormones, analgesics, prostaglandin inhibitors, prostaglandin synthetase inhibitors, leukotriene receptor antagonists, essential fatty acids, sterols, anti-inflammatory agents, vasodilators, chemotherapeutic agents, and agents to treat infertility.

These beneficial agents promote epithelial health in the vaginal region. The idea is to modulate the vaginal environment to enhance the wellness of this anatomical region. These benefits can be rather simple, for example increasing comfort by providing moisturization and/or lubricity. These benefits can also be more complex, for example modulating epithelial cell function to address vaginal atrophy. The beneficial therapeutic agents may reduce negative sensations such as stinging, burning, itching, etc, or introduce positive sensations to improve comfort.

For example, many therapeutic benefits have been ascribed to a large number of different botanical preparations. Preparations may include water-in-oil emulsions, oil-in-water emulsions, gel, liquid, dispersion, powder, and anhydrous systems, ointment, or salve, such as a botanical oil in an anhydrous base (e.g., petrolatum), or polyethylene glycol based systems. Also, botanicals are often prepared or extracted under conditions to generate water-soluble or oil-soluble extracts. These extracts are usually compositionally different and may have different skin and vaginal health benefits. Processing conditions will have an effect on the type of formulation that can be used and this will restrict the type of botanical (water or oil type) selected. Therefore, wide ranges of botanicals have utility in this invention. Botanicals can possess a variety of actives and activities that can include, but are not necessarily limited to, analgesics, antimicrobials, pro-biotic agents, anti-inflammatory compounds, anti-virals, enzymes, enzyme inhibitors, enzyme substrates, enzyme cofactors, ions, ion chelators, lipids, lipid analogs, lipid precursors, hormones, inflammatory mediators, inflammatory agonists, oxidants, antioxidants, humectants, growth factors, sugars, oligosaccharides, polysaccarides, vasodilators, and potential combinations thereof. It is understood that, for the purposes of this invention, the botanicals can be combined with any number of non-botanical active ingredients as well.

The dosage form 64 can be any drug, excipient, formulation, compound, or combination thereof that is desirable to introduce into the vaginal cavity. The dosage form 64 can be combined with any absorbent tampon design. The dosage form 64 is preferably positioned at the distal end of the tampon. The dosage form 64 can be designed to partially cover the absorbent structure on the tip of the tampon or fully cover the tampon tip. The medicated tampons can be formed into specific shapes such as various cup shapes to enhance the drug contact area with the cervix, posterior formix, vaginal epithelium areas, or conformance to other anatomical areas within the vaginal cavity.

In one embodiment the formulation including a therapeutic agent is produced in tablet, capsule, or suppository form. In alternate embodiments, the tablet, suppository, or capsule may be designed to melt at approximately body temperature, or to dissolve or otherwise disperse in the presence of sufficient humidity or appropriate chemistry, such as a suitable pH. The physical form of the formulation including a Therapeutic agent is referred to herein as a dosage form 64, although the dosage form 64 may be in any suitable form including, but not limited to, tablets, capsules, suppositories, disks, lozenges, and the like.

The dosage form 64 may be provided with one or more layers, or may be formed with more than one therapeutic agent. The one or more layers may also include a beneficial agent, an excipient, a carrier component, or some combination of these or other ingredients. In its simplest form, the ingredient or ingredients of the dosage form are mixed into a single homogeneous layer. The dosage form may also be formed with two layers, where a first layer includes a therapeutic agent and may be referred to as an active layer, and where a second layer includes a different therapeutic agent, or one of the other ingredients described herein. If more than one therapeutic agent is provided, the therapeutic agents may be commingled, or may be in separate layers. If more than one therapeutic agent is provided, the therapeutic agents may be arranged such that one therapeutic agent is released in greater quantity before the other therapeutic agent is generally released, in a time-release manner. The dosage form 64 may also be provided with additional layers including one or more ingredients, as dictated by the use of the dosage form. To summarize, each layer may contain one or more ingredients, including one or more therapeutic agents, one or more beneficial agents, one or more excipients, one or more carrier components, or a combination of any of these.

The second layer or a succeeding layer may also be an attachment layer formed from ingredients specifically chosen to assist in attaching the dosage form 64 to the tampon body 50. An ingredient or ingredients for an attachment layer may be chosen for its/their propensity to melt or react such that the dosage form 64 can be attached to the tampon body 50. The attachment layer ingredient or ingredients may also be chosen for its/their propensity to melt at body temperature, ensuring that the dosage form 64 is separated from the tampon body 50 during use.

In one example, SUPPOCIRE-brand suppository base may be used as an attachment layer. In an alternate embodiment, the attachment layer may contain one or more ingredients that are the same as the ingredient or ingredients of the first layer. In another alternate embodiment, the ingredient or ingredients of the attachment layer are different from that or those of the first layer. In another alternate embodiment, the attachment layer may contain material that is similar to but has properties differentiated from the material of the active layer. For example, the attachment layer may have a higher or lower melting point than the active layer, such that the attachment layer melts more slowly or more quickly than the active layer.

The term layer as used herein does not solely refer to a stack of vertically-aligned, generally horizontal planar ingredient disks. Layer may refer to any sort of zoning or distribution of ingredients, including vertical slices, asymmetrically-loaded zones, or isolated regions or pockets of ingredients. In other words, layer may refer to any nonhomogeneous distribution of ingredients within the dosage form 64.

The layers may also contain ingredients that facilitate therapeutic agent absorption or provide other differentiated properties to enhance product performance. In one embodiment, the excipient ingredients in one layer may have a different melt point from one or more adjacent layers, which advantageously provides a differentiated release of therapeutic agents or carrier component excipient ingredients throughout a temperature range. The dosage form 64 may also be provided with one or more coatings, such as a surfactant.

The dosage form may be manufactured by homogeneously mixing the necessary ingredients and depositing them into a form such that a dosage form 64 is created. The dosage from 64 may be shaped and manufactured by any suitable method. In the case of a dosage form having more than one layer, the first layer may be deposited and allowed to cool, dry, or set, as appropriate, before the second layer is deposited on the first layer. Succeeding layers may be deposited in the same way until the desired dosage form 64 is created.

The dosage form 64 may be produced by the same manufacturer as the manufacturer of the tampon. The dosage form 64 may also be produced by a separate manufacture and provided to the tampon manufacturer in any suitable manner. The dosage form 64 may be pre-manufactured in any of these ways. As an example, a dosage form manufacturer with a facility specifically designed for pharmaceutical manufacturing can produce the dosage forms 64 under conditions such that homogeneity, concentration, and purity of the dosage form 64 are closely controlled, and such that production is in accordance with applicable regulations. The dosage form 64 can then be sealed and shipped to the tampon manufacturer. The tampon manufacturer can then apply the dosage form 64 to a tampon under appropriately-controlled conditions. In this manner, the dosage form 64 is produced by a manufacturer with appropriate experience, and the tampon manufacturer is relieved of establishing a pharmaceutical-production facility.

In one method of assembling the therapeutic tampon system 10, a portion of the dosage form 64 is heated to partially melt the excipient in that portion. In alternate embodiments, all or a portion of the dosage form 64 may be partially or fully melted. The dosage form 64 is then abutted with the tampon body 50 such that the partially-melted portion is applied with appropriate pressure to engage the tampon body. The partially-melted portion then re-solidifies, becoming attached to the tampon body 50. In one embodiment, the dosage form 64 partially absorbs into the tampon body 50 and is thereby mechanically engaged with the fibers of the tampon body 50. In another embodiment, the dosage form 64 is thereby chemically engaged with the tampon body 50.

In one embodiment described herein, a pre-manufactured dosage form is attached to the tampon body 50 using pressure, a heat source, or a combination of pressure and heat, to partially or fully melt a portion of the dosage form itself. In an alternate embodiment, this attachment could be accomplished in a manufacturing environment by introducing a small amount of heated, melted SUPPOCIRE-brand suppository base onto the distal end 58 of the tampon body 50 just prior to introducing the dosage form 64 onto the distal end 58. The heat contained in the melted SUPPOCIRE-brand suppository base partially melts the dosage form and creates a secure bond when both liquids cool and harden.

In an alternate method of assembly, the dosage form 64 is at least partially coated with a suitable biologically-compatible adhesive as is known in the art and then abutted with the tampon body 50 such that the dosage form 64 is affixed to the tampon body 50.

In various embodiments, the tampon 22 may include a recess, a dimple, a depression, a concavity, or a reservoir (generically a recess) 66 at the distal end 58 (see FIG. 2). The recess 66 is designed to accommodate the dosage form 64, which can be applied to the recess by any method described herein or by any other suitable method. In an alternate embodiment, the recess 66 may be formed as a simple dimple. In other alternate embodiments, the tampon 22 may be formed into any suitable shape to promote contact between the tampon 22 and anatomical structures such as the vaginal epithelium, the posterior formix, the cervix, or other structures.

In alternate embodiments, the dosage form 64 may be formed in any shape to promote attachment to tampon 22 and/or to promote contact with anatomical structures such as the vaginal epithelium, the posterior formix, the cervix, or other structures.

The therapeutic agent delivery system 10 may also include carrier components to promote the functionality of the therapeutic agent. For example, the carrier components may assist the therapeutic agent in absorbing into, or adhering onto, the tampon body 50. The carrier components may assist the release of the therapeutic agent, or assist in the absorbency of the therapeutic agent into the vaginal epithelium. The use of excipients to facilitate the formulation, delivery, stability, and aesthetic properties of a drug delivery system is well known to those familiar with the art.

In use, and referring to FIG. 2, the applicator 11 functions because the second member 18 is telescopically movable relative to the first member 14. As the second member 18 is pushed into the first member 14, the tampon 22 is forced forward against the pleats or petals 36. The contact by the tampon 22 causes the pleats 36 to radially open to a diameter that is sufficient to allow the tampon 22 to be expelled from the first member 14. With the tampon 22 properly positioned in the woman's vaginal cavity, the tampon applicator 11 is withdrawn and properly discarded.

Once the tampon 22 is properly positioned in the woman's vaginal cavity, the tampon body 50 may absorb menses and other bodily fluids, and the tampon body 50 may also deliver the therapeutic agent to the vaginal epithelium. From there, the therapeutic agent is transferred to the uterus by normal bodily functions to relieve the condition to be treated.

The invention has been described with reference to various specific and illustrative embodiments and techniques. However, it should be understood that many variations and modifications may be made while remaining within the spirit and scope of the invention.

Accordingly, this invention is intended to embrace all such alternatives, modifications and variations that fall within the spirit and scope of the appended claims.

We claim:

1. A tampon adapted to deliver a therapeutic agent, the tampon comprising:
   a tampon body having a distal end; and
   a dosage from affixed to the distal end of the tampon body, wherein the dosage form includes a formulation including a therapeutic agent, wherein the dosage form comprises a first active layer including active layer material and an attachment layer including attachment material, and wherein the therapeutic agent is a botanical selected from the group consisting of Agnus castus, aloe vera, comfrey, calendula, dong quai, black cohosh, chamomile, evening primrose, Hypericum perforatum, licorice root, black currant seed oil, St. John's wort, tea extracts, lemon balm, capsicum, rosemary, Areca catechu, mung bean, borage seed oil, witch hazel, fenugreek, lavender, soy, Vaccinium extracts, cranberries, blueberries, azaleas (Rhododendron spp.), red onion skin, short and long red bell peppers, Beta vulgatis (beet) root extract, capsanthin, whortleberry, lingenberry, chokeberry, sweet rowan, rowanberry, seabuckhrouberry, crowberry, strawberries, and gooseberries.

2. A tampon adapted to deliver a therapeutic agent, the tampon comprising:
   a tampon body having a distal end; and
   a dosage form affixed to the distal end of the tampon body, wherein the dosage form includes a formulation including a therapeutic agent, wherein the dosage form comprises a plurality of layers including an attachment layer and wherein the dosage form is affixed to the body by partially melting the attachment layer.

3. The tampon of claim 2, wherein the partially melted attachment layer partially absorbs into the tampon body.

4. A tampon adapted to deliver a therapeutic agent, the tampon comprising:
   a tampon body having a distal end; and
   a dosage form affixed to the distal end of the tampon body, wherein the dosage form includes a formulation including a therapeutic agent, wherein the dosage form comprises a plurality of layers, and wherein the dosage form is affixed to the tampon body using a biologically-compatible adhesive.

5. A method for manufacturing a medicated tampon adapted to deliver a therapeutic agent, the method comprising:
   manufacturing a tampon body having a distal end;
   producing a dosage form having a plurality of layers including an attachment layer, wherein the dosage form includes a formulation including a therapeutic agent; and
   affixing the dosage form to the distal end of the tampon body, including partially melting the attachment layer to affix the dosage form.

6. A method for manufacturing a medicated tampon adapted to deliver a therapeutic agent, the method comprising:
   manufacturing a tampon body having a distal end;
   producing a dosage form having a plurality of layers, wherein the dosage form includes a formulation including a therapeutic agent; and
   affixing the dosage form to the distal end of the tampon body, including using a biologically-compatible adhesive to affix the dosage form.

7. The tampon of claim 2, wherein a first layer is a first active layer including active layer material, and wherein a second layer is an attachment layer including attachment material.

8. The tampon of claim 7, wherein the first active layer includes a therapeutic agent end wherein the therapeutic agent is selected from the group consisting of nonsteroidal anti-inflammatory drugs (NSAIDs), prostaglandin inhibitors, COX-2 inhibitors, local anesthetics, calcium channel blockers, potassium channel blockers, β-adrenergic agonists, vasodilators, leukotriene blocking agents, smooth muscle inhibitors, and drugs capable of inhibiting dyskinetic muscle contraction.

9. The tampon of claim 8, wherein the NSAID is selected from the group consisting of aspirin, ibuprofen, indomethacin, phenylbutazone, bromfenac, sulindac, nabumetone, ketorolac, mefenamic acid, and naproxen.

10. The tampon of claim 8, wherein the COX-2 inhibitor is selected from the group consisting of celecoxib, meloxicam, rofecoxib, end flosulide.

11. The tampon of claim 8, wherein the local anesthetic is selected from the group consisting of lidocaine, mepivacaine, etidocaine, bupivacaine, 2-chloroprocaifle hydrochloride, procaine, and tetracaine hydrochloride.

12. The tampon of claim 8, wherein the calcium channel blocker is selected from the group consisting of diltaizem, israpidine, nimodipine, felodipine, verapamil, nifedipine, nicardipine, and bepridil.

13. The tampon of claim 8, wherein the potassium channel blocker is selected from the group consisting of dofetilide, e-4031, imokalant, semetilide, ambasilide, azimilide, tedisamil, rp58866, sotalol, piroxicam, and ibutilide.

14. The tampon of claim 8, wherein the β-adrenergic agonist is selected from the group consisting of terbutaline, salbutamol, metaproterenol, and ritodrine.

15. The tampon of claim 8, wherein the vasodilator is selected from the group consisting of nitroglycerin, isosorbide dinitrate, and isosorbide mononitrate.

16. The tampon of claim 7, wherein the first active layer includes a beneficial agent.

17. The tampon of claim 16, wherein the beneficial agent is selected from the group consisting of a botanical, a vitamin, calcium, magnesium, a hormone, a prostaglandin synthetase inhibitor, a leukotriene receptor antagonist, an essential fatty acid, a sterol, an anti-inflammatory agent, a chemotherapeutic agent, and an agent to treat infertility.

18. The tampon of claim 7, wherein the attachment material is different from the active layer material.

19. The tampon of claim 7, wherein the attachment material is similar to but has a property differentiated from the active layer material.

20. The tampon of claim 7, wherein the first active layer includes a carrier component.

21. The tampon of claim 7 wherein a third layer is a second active layer, and wherein the first active layer and the second active layer are adapted such that the second active layer is substantially released from the dosage form prior to the substantial release of the first active layer.

22. A method for manufacturing a medicated tampon adapted to deliver a therapeutic agent, the method comprising:
    manufacturing a tampon body having a distal end;
    producing a dosage form having a plurality of layers includes forming a first active layer including active layer material, and forming an attachment layer including attachment material, wherein the dosage form includes a formulation including a therapeutic agent, the therapeutic agent being incorporated in the first active layer; and
    affixing the dosage form to the distal end of the tampon body by partially melting the attachment layer.

23. The method of claim 22, further comprising selecting the attachment material and the active layer material such that the attachment and active layer materials are different.

24. The method of claim 22, further comprising selecting the attachment material and the active layer material such that the attachment and active layer materials are similar but have a property that is differentiated between the two materials.

25. The method of claim 22, wherein the producing act includes incorporating a beneficial agent in the first active layer.

26. The method of claim 22, wherein the producing act includes incorporating a carrier component in the first active layer.

27. The method of claim 22, wherein the producing act includes forming a second active layer.

28. The method of claim 27, wherein the producing act includes adapting the first active layer and the second active layer is substantially released from the dosage form prior to the substantial release of the first active layer.

29. The method of claim 22, wherein the affixing act includes allowing the partially melted attachment layer to partially absorb into the tampon body.

30. A tampon adapted to deliver a therapeutic agent, the tampon comprising:
    a tampon body having a distal end; and
    a dosage form affixed to the distal end of the tampon body by partially melting the dosage form, wherein the dosage form includes a formulation including a therapeutic agent, wherein the dosage form is pre-manufactured, and wherein the dosage form comprises a plurality of layers.

* * * * *